United States Patent [19]

Kiyota et al.

[11] Patent Number: 5,067,979

[45] Date of Patent: * Nov. 26, 1991

[54] SINTERED BODIES AND PRODUCTION PROCESS THEREOF

[75] Inventors: Yoshisato Kiyota; Junichi Ohta; Hiroshi Ohtsubo; Shigeaki Takajo, all of Chiba, Japan

[73] Assignee: Kawasaki Steel Corporation, Japan

[ * ] Notice: The portion of the term of this patent subsequent to Oct. 23, 2007 has been disclaimed.

[21] Appl. No.: 549,491

[22] Filed: Jul. 6, 1990

Related U.S. Application Data

[62] Division of Ser. No. 393,765, Aug. 14, 1989, Pat. No. 4,964,907.

[51] Int. Cl.$^5$ ............................................. C22C 29/00
[52] U.S. Cl. ........................................ 75/243; 75/230; 75/246; 252/62.55; 419/23; 419/36; 419/37; 419/54; 419/57
[58] Field of Search .......................... 75/246, 243, 230; 419/23, 36, 37, 54, 57; 252/62.55

[56] References Cited

U.S. PATENT DOCUMENTS 4,564,407 10/1990 Kiyoto et al. .......................... 419/23
4,601,875 7/1986 Yamamoto et al. ................... 419/23
4,797,251 1/1989 Sakuramoto et al. ................ 419/54

Primary Examiner—Stephen J. Lechert, Jr.
Attorney, Agent, or Firm—Austin R. Miller

[57] ABSTRACT

A process is provided for the production of a sintered body. The process includes the following consecutive steps: i) mixing and kneading one or more metal powders and/or one or more alloy powder with a binder into a compound, said metal and alloy powders having an average particle size not greater than 30 μm, ii) injection-molding the compound into a green body; iii) debinding the green body to form a debound body; and iv) subjecting the debound body to a first-stage sintering at 1,050°–1,250° C. in a reduced-pressure atmosphere and then to second-stage sintering at a temperature in a range of 1,100°–400° C. which is higher than that of the first-stage sintering. This process can provide sintered Ti bodies and sintered magnetic bodies of the Fe-Si type, which have a density ratio of at least 95%.

5 Claims, No Drawings

SINTERED BODIES AND PRODUCTION PROCESS THEREOF

This is a division, of application Ser. No. 07/393,765, filed Aug. 14, 1989, U.S. Pat. No. 4,964,907.

BACKGROUND OF THE INVENTION

The present invention relates to sintered bodies produced by a powder metallurgical process. In particular, this invention is concerned with sintered bodies, such as sintered magnetic bodies of the Fe-Si type having excellent a.c. alternating current (a.c.) characteristics, and their production process.

Prior to this application, one or more of the inventors of this invention and others already have filed "Sintered FeCo Type Magnetic Materials and Production Process Thereof (PCT JP89/00537)" and "Stainless Steel Sintered Materials and Production Process Thereof (PCT JP89/00633)".

In these applications, the inventors have described a superior sintered Fe-Co magnetic body which has low C and O contents and high density, a sintered stainless steel body which has high density and high corrosion resistance, and the method of production of these sintered bodies.

Ti has a smaller specific gravity as compared to steel material but its strength is by no means inferior to steel, so that it is employed as a material for a variety of aircraft parts. It is also used for such medical purposes as prostheses and for orthopaedic surgery because it has good compatibility with human tissues, and is without deleterious effects to the human body.

Ti parts have heretofore been formed from Ti ingots. These conventional Ti parts however incur a high production cost and their productivity is low, since their machining yield is low. It has been known that the use of a powder metallurgical process makes it possible to produce sintered Ti bodies at a low cost and with high productivity. Ti is however a very active metal so that the surfaces of its particles tend to be covered with an oxide. This has led to the problem that high-density and low-impurity bodies are difficult to obtain regardless what conventional sintering process is employed. Further, any attempt at using a high-purity Ti powder of low C and 0 contents inevitably results in a high material cost, whereby the inherent economy of powder metallurgy is impaired.

Injection molding requires a binder in addition to a powdered raw material. It is however difficult to completely remove the binder in a subsequent step, so that the resulting sintered body has high C and 0 contents. No sintered high-density bodies can therefore be obtained.

Hot isostatic pressing is also recognized as a process for the production of sintered high-density bodies. This process however requires a complex and expensive apparatus and is hence accompanied by the problems of requiring a longer working time and being economically disadvantageous.

Y. Kaneko et al. at Faculty of Science and Engineering, Ritsumeikan Univ. have reported on the injection molding of titanium powder (Abstracts of Papers, Spring Meeting of Japan Society of Powder and Powder Metallurgy, 1988, pp 126 to 127). According to the abstract, a sintered body having a density ratio of 92% was obtained from Ti powder, by injection-molding the powder together with a binder and sintering the molded body at 1300° C. for two hours under a reduced pressure of 0.01 Torr. In addition, it is obvious that this sintered body has a fairly high oxygen contents, because the abstract also describes formation of $TiO_2$ based on the results of X-ray diffraction analysis and microscopic observation of the structure.

On the other hand, Fe-Si alloys feature high electrical resistivity among soft magnetic materials. Assisted further by their low core losses, they are employed widely for a.c. applications.

There is however a limitation imposed on the application of sintered bodies of such Fe-Si alloys due to the low compressibility inherited from the hard and brittle properties of the alloys. This tendency is especially remarkable in the case of Fe-Si alloys which contain Si in a proportion of about 3 wt. % or higher.

"Sintering Behavior, Mechanical and Magnetic Properties of Sintered Fe-Si Materials" have been described in the International Journal of Powder Metallurgy & Powder Technology Vol. 20, No. 4, 1984. In this report, the authors described "Fe-Si (sintered) materials that were prepared by varying both the starting Fe powder and the way of Si addition. Water atomized iron powder mixed with pre-alloyed FeSi30 proved to be the most successful.".

As a method for improving moldability, injection molding using an organic binder is regarded as a promising candidate because the hardness of a powder is practically immaterial. But when a metal powder is shaped by injection molding and then sintered, there is no method known for eliminating C, which is derived from the organic binder, without extreme oxidation of a highly oxidative element such as Si. It has hence been impossible to provide a sintered body excellent in a.c. magnetic characteristics.

SUMMARY OF THE INVENTION

An object of this invention is to solve the above-described problems and to provide a sintered high-density and low-impurity Fe-Si body by using a conventional vacuum furnace without need for any special apparatus and also to provide a production process thereof.

Another object of this invention is to provide a sintered magnetic body of the Fe-Si type, said body having excellent a.c. magnetic characteristics, and also a process for producing the above sintered body by using an injection molding method and removing, without extreme oxidation, C derived from an organic binder.

In one aspect of this invention, there is thus provided a process for the production of a sintered body, which comprises the following steps:

(i) mixing and kneading at least one powder selected from the group which consists of one or more metal powders and one or more alloy powders with a binder into a compound, said metal and alloy powders having an average particle size not greater than 30 μm;

(ii) injection-molding the compound into a green body;

(iii) debinding the green body to form a debound body; and (iv) subjecting the debound body to first-stage sintering at 1,050°–1,250° C. in a reducing or reduced-pressure atmosphere and then to second-stage sintering at a temperature in a range of 1,100°–1,400° C. which is higher than the temperature of the first-stage sintering.

In the above processes, it is preferable to adjust the C/O molar ratio of the debound body to 0.5-3.0 before conducting the first-stage sintering.

In a further aspect of this invention, there is also provided a process for the production of a sintered magnetic body of the Fe-Si type, which comprises the following steps:

(i) mixing and kneading at least one powder selected from the group which consists of one or more Fe-Si alloy powders, an Fe powder and a Si powder with a binder into a compound to give a final composition which comprises 1.5-6.5 wt. % of Si and the balance substantially of Fe, said alloy and metal powders having an average particle size of 3-25 μm;

(ii) injection-molding the compound into a green body;

(iii) debinding the green body to form a debound body; and (iv) subjecting the debound body to first-stage sintering at 1,050°-1,250° C. in a reducing atmosphere or a reducedpressure atmosphere not higher than 0.1 Torr and then to second-stage sintering at a temperature at least 50° C. higher than the temperature of the first-stage sintering.

It is preferable to adjust the C/O molar ratio of the debound body to 0.5-3.0 before conducting the first-stage sintering. It is also preferable to conduct the second-stage sintering in an inert gas atmosphere of at least 30 atm. In addition, when the second-stage sintering is conducted in an atmosphere of at least 30 atm, the alloy powders and metal powders may preferably have an average particle size of 10-25 μm.

In a still further aspect of this invention, there is also provided a sintered magnetic body of the Fe-Si type consisting essentially of 1.5-6.5 wt. % of Si, up to 0.5 wt. % of O, up to 0.03 wt. % of C, and the balance of Fe and imperative impurities and having a density ratio of at least 95%.

The term "average particle size" as used herein means the particle size at which the cumulative volume from the side of finer particles reaches 50% and is measured by a microtracking particle size analyzer.

On the other hand, the term "density ratio" means the ratio of the bulk density to a corresponding true density, and is measured in accordance with the underwater weight measuring method (Archimedean method).

DETAILED DESCRIPTION OF THE INVENTION

A description will next be made of the process of this invention for the production of a sintered magnetic body of the Fe-Si type. According to the production process of this invention, a metal powder is mixed and kneaded with an organic binder, followed by injection molding, debinding and sintering. In particular, a principal feature of the process of this invention resides in the adoption of injection molding in place of compression forming which has generally been relied upon. In compression forming, the powdered raw material is limited to a coarse powder having low sinterability. Compared to compression forming, injection molding is advantageous in that a fine powder having high sinterability can be used. This has made it possible to improve the conventional low magnetic characteristics.

The present inventors have found that the magnetic characteristics of a sintered body are closely correlated to the particle size of the powdered raw material. The average particle size of the powdered raw material governs the density of the sintered body. Average particle sizes in excess of a predetermined upper limit cannot provide any sintered body according to this invention.

Although the particle size of the powdered raw material varies depending on the manner of sintering, the average particle size is generally required to fall within a range of 3-25 μm. First, an average particle size of 3-9 μm is preferred when sintering is conducted by usual heating alone. When pressure-assisted sintering involving simultaneous heating and gas pressurization is applied, 10-25 μm is preferred. When sintering is effected only by heating, a greater average particle size results in a lower density ratio of the sintered body. Average particle sizes greater than 9 μm cannot give the density ratio of 95%. Further, average particle sizes greater than 25 μm cannot attain the density ratio of 90%. However, so long as the density ratio of the sintered body is greater than 90%, the pores of the sintered body are in the form of closed pores so that the density ratio can be increased to 95% or higher by pressure-assisted sintering.

As a matter of fact, a significant improvement can be observed in the density ratio upon pressure-assisted sintering where the average particle size is 10 μm or greater, so that a density ratio rather greater than that available from the use of a powder having an average particle size smaller than 10 μm may be obtained.

On the other hand, average particle sizes greater than 25 μm can by no means achieve any density ratio of 95% or greater, thereby failing to provide a sintered body according to this invention. The upper limit of the average particle size has therefore been set at 25 μm. Further, powders having an average particle size smaller than 3 μm are expensive and hence uneconomical. These powders have therefore been excluded.

A description will next be made of conditions for the sintering.

It is indispensable to conduct the sintering in two stages.

The first-stage sintering must be conducted in a hydrogen-containing gas, which is a reducing atmosphere, or in a reduced-pressure atmosphere of 0.1 Torr or lower. Otherwise, surface oxygen of the powdered raw material and carbon derived from the remaining binder cannot be eliminated and no sintered high-purity body can hence be obtained. It is also necessary to conduct the first-stage sintering at 1,050°-1,250° C. If the sintering temperature is lower than the lower limit of this range, the reaction which is supposed to take place between the atmosphere and the powdered raw material for the elimination of impurities does not proceed effectively. On the other hand, sintering temperatures higher than the upper limit allow interparticle sintering of the powder to proceed faster than the reaction for the elimination of the impurities so that the impurities cannot be eliminated. Since these impurities are eliminated as water vapor or carbon dioxide gas, the loss of gas flow pores poses a serious problem. Special care must be paid in this regard because a green body is formed of fine particles and its flow pores are inherently small. In addition, the temperature of the first-stage sintering is the temperature at which the progress of sintering begins to accelerate. Since this temperature also varies depending on the particle size of the powdered raw material, it is desirable to choose the temperature of the first-stage sintering on a lower side when the average particle size is small and on a higher side when the average particle size is large, both from the temperature range of the present invention.

The sintering period is the time required until the contents of C and 0 reach equilibrium at the sintering temperature employed. It is usually in a range of from 20 minutes to 4 hours. The sintering time can be easily determined by conducting several trial experiments.

The second-stage sintering of this invention will next be described.

The second-stage sintering no longer requires any reactive gas because it is applied to densify the sintered body which has been subjected to purification and pore closure in the first-stage sintering step. Therefore, the atmosphere gas may preferably be limited to an inert gas. Further, the temperature must be at least 50° C. higher than the sintering temperature of the first-stage sintering.

The lower limit of the temperature has been set at a temperature at least 50° C. higher than the first-stage sintering temperature, because the first-stage sintering temperature is set at the temperature at which the sintering speed begins to accelerate and is not high enough for densification. When a reduced-pressure atmosphere is used in the first-stage sintering step, a compositional distribution occurs in the surface of the resultant sintered body because of differences in vapor pressure among the constituent elements. Even in an atmosphere of a reducing gas, a compositional distribution may also occur between the surface of a sintered body or each particle, said surface being exposed to the gas, and the inside thereof. This compositional distribution occurs by differences in atomic diffusion velocity within the sintered body. It is therefore necessary to allow the homogenization treatment to proceed promptly at a temperature at least 50° C. higher than the temperature of the first-stage sintering, namely, in a temperature range capable of realizing a higher diffusion velocity in an atmosphere of atmospheric pressure of higher, at which the constituent elements do not evaporate, or in an atmosphere in which absolutely no chemical reaction takes place.

The upper limit of the second-stage sintering temperature is the temperature at which the crystal grain size does not become coarse beyond necessity and no melting begins to take place. The more suitable temperature range is 1,200°–1,350° C.

Even when pressure-assisted sintering is conducted in the above second-stage step, the lower limit of the temperature should be at least 50° C. higher than the temperature of the first-stage sintering. This lower limit temperature is the temperature which the sintering velocity begins to increase, and is correlated to the temperature set for the first-stage sintering. Above this temperature, pressure-assisted sintering becomes effective. Further, as has been described above, it is necessary to allow a homogenization treatment to proceed promptly in this step in order to eliminate the compositional distribution as occurred in the first-stage sintering. Pressure-assisted sintering also requires a similar upper limit temperature to pressureless sintering. The pressure required for pressurization ranges from 30 atm to 150 atm. Pressures lower than 30 atm cannot bring about any significant difference compared to pressureless sintering, while the use of a gaseous medium higher than 150 atm leads to a tremendous increase in the initial cost.

The period of the second-stage sintering is the time required until the sintered density and chemical compositional distribution reach equilibrium at the sintering temperature employed. It generally ranges from 20 minutes to 2 hours. It can be easily chosen through several trial experiments.

By limiting the sintering method as described above, it is possible for the first time to economically produce sintered Fe-Si bodies of high magnetic characteristics by virtue of injection molding.

The starting powdered raw material, which constitutes the powdered raw material of this invention, is used after adjusting its particle size to a suitable level by sifting or grinding it subsequent to its formation by the high-pressure water atomizing method, the reducing process, the carbonyl process or the like. As the powdered raw material in this invention, such starting powdered raw materials can be used either singly or in combination. Regarding the purity of the powdered raw material, it may contain impurities other than C and 0, which can be eliminated in the course of sintering, at practically-ignorable level. In general, powders containing Fe and Si in a total proportion of 97–99 wt. % can be used.

The powdered raw material is mixed and kneaded with a binder into a compound, which is then shaped by a known injection molding method. In particular, injection molding is effective for parts of an intricate shape.

Usable binders are similar to those already discussed in patent application Ser. No. 393,765 filed Aug. 14, 1989, now U.S. Pat. No. 4,964,907 granted Oct. 23, 1990, with respect to sintered Ti bodies.

The amount of the binder to be added may range from 40 vol.% to 60 vol.% of the total volume (the remaining volume corresponds to the starting metal powder). This can be adjusted in view of the forming readiness of the compound obtained and the debinding property of the green body obtained.

A batchwise or continuous kneader can be used for the mixing and kneading of the metal powder and the binder. After mixing and kneading, the compound is granulated by means of a pelletizer, a granulator or the like so that a forming feed-stock can be obtained.

The forming feed-stock can be formed by means of a conventional injection molding machine for plastics.

The green body thus obtained is then subjected to a debinding treatment in atmosphere or in a surrounding gas.

After the debinding treatment, sintering is conducted as described above so as to achieve reduction of C and O contents and high densification.

In addition, the C and O contents of the sintered final body may be adjusted as needed. The C and O contents may be increased or decreased by adjusting the molar C/O ratio of the debound body. The C content can be reduced by making the molar C/O ratio smaller, while the 0 content can be lowered by making the molar C/O ratio greater.

It is preferable to adjust the molar C/O ratio to 0.5–3.0, more preferably to 0.6–1.0, because these ranges can easily provide sintered bodies of low contents of C and O in the range of this invention.

Adjustment of the C/O molar ratio can be achieved, for example, by controlling the C and O contents in the powdered raw material, by increasing or decreasing the degree of debinding, and/or by applying an oxidation treatment after the debinding. Reduction of the overall level of the C and O contents, said level being equivalent to the product of the C content and the 0 content, can be effected by modifying the atmosphere for the first-stage sintering. When a reduced-pressure atmosphere is used, this can be achieved by reducing the pressure. When a reducing atmosphere is used, this can be attained by improving the purity of the atmosphere gas.

A description will next be made of the sintered magnetic body of the Fe-Si type according to this invention. The sintered magnetic body of the Fe-Si type consists essentially of 1.5-6.5 wt. % of Si, up to 0.5 wt. % of 0, up to 0.03 wt. % of C, and the balance of Fe and imperative impurities and has a density ratio of at least 95%.

The composition of the sintered body of this invention has been limited as described above for the following reasons.

Si: 1.5-6.5 wt. %

When added to Fe, Si can improve the electrical resistivity. Proportions smaller than 1.5 wt. % are however too little to draw out its effect to a significant extent. In addition, Si can also improve magnetic permeability. Its permeability-improving effect however drops abruptly when the proportion of Si exceeds 6.5 wt. %. The proportion of Si has therefore been limited to 1.5-6.5 wt. %.

0: up to 0.5 wt. %: C: up to 0.03 wt. %

C and 0 give deleterious influences to magnetic characteristics, especially to coercive force (Hc) and maximum magnetic permeability ($\mu$max).

However, when an element highly susceptible to oxidation such as Si is contained, it is practically impossible to simultaneously reduce the contents of 0 and C, which have been derived respectively from the powdered raw material and the organic binder added to convert the powdered raw material into the compound suitable for injection molding, in the sintering atmosphere. The principal object was therefore placed on the reduction of the content of C which adversely affects magnetic characteristics in particular. Namely, magnetic characteristics undergo substantial deteriorations when the content of C exceeds 0.03 wt. %. Therefore, the upper limit of the C content has been set at 0.03 wt. %.

On the other hand, magnetic characteristics are also deteriorated significantly when the 0 content exceeds 0.5 wt. %. Therefore, the upper limit of the 0 content has been set at 0.5 wt. %. It is preferable to limit the contents of 0 and C to 0.1 wt. % or less and 0.03 wt. % or less, respectively.

Further, when the 0 content is in the range of 0.03 wt. % to 0.5 wt. %, a sintered body which has the C content of not more than 0.03 wt. % is easily obtained. Therefore an O content of 0.03 wt. % to 0.5 wt. % is preferable in industrial processes.

Density Ratio: at least 95%

Magnetic flux density is proportional to the density ratio of the sintered body. When the density ratio is smaller than 95%, the magnetic flux density is reduced substantially so that the resultant sintered body may not be found superior to a sintered body obtained by compression molding which is a competitive forming method.

Accordingly, the lower limit of the density ratio has been set at 95%.

Introduction of the above limitations has made it possible for the first time to obtain sintered Fe-Si bodies of this invention, which have excellent magnetic characteristics.

EXAMPLES

This invention will hereinafter be described specifically on the basis of the following examples.

EXAMPLES 1-3 AND COMPARATIVE EXAMPLES 1-3

Ti powders whose average particle sizes are shown in Table 1 were provided as powdered raw materials. Each of the Ti powders was added and mixed with a thermoplastic resin and a wax as binders. The resultant mix was kneaded into a compound by a dispersion mixer.

The compound was granulated to obtain a forming feedstock.

The forming feed-stock was formed into a plate-like green body 2 mm thick by means of an injection molding machine. The green body was heated to 600° C. at a heating rate of 10° C./hr in a nitrogen atmosphere. Thereafter, the temperature and the oxygen potential in the atmosphere were controlled to adjust the C/O molar ratio in the body to 0.5-1.0.

The thus-debound body was maintained for at least 1 hour in a reduced pressure atmosphere ($<10^{-3}$ Torr) at the temperature given in Table 1, and was then heated to 1,300° C., at which it was maintained for 3 hours.

After cooling, its density ratio was determined from its density measured by the Archimedean method and a measurement datum of its true density. Further, the contents of C and O in the sintered body were analyzed.

The results are summarized in Table 1.

Examples 1 and 2 gave sintered bodies of high density and low impurity because the average particle size of the powdered raw material was 10 $\mu$m and the first-stage sintering temperature was controlled at 1,080° C. or 1,150° C.

In Example 3, the average particle size of the powdered raw material was 25 $\mu$m and hence greater compared with Examples 1 and 2. Accordingly, Example 3 gave a sintered body having still lower C and 0 contents although the density ratio was 95%.

In Comparative Example 1, the first-stage sintering temperature was as low as 1,000° C. The sintering was switched to high-temperature sintering probably before the elimination of C and 0 had proceeded sufficiently. This seems to be responsible to the high C and 0 contents of the sintered final body.

In Comparative Example 2, the first-stage sintering temperature was as high as 1,250° C. This appears to have promoted the closure of pores, whereby CO and $CO_2$ gases were probably trapped. This seems to be responsible for the high C and 0 contents of the sintered final body.

In Comparative Example 3, the first-stage sintering temperature was 1,150° C. and the elimination of C and 0 proceeded. However, the powdered raw material had the average particle size of 35 $\mu$m and was a coarse powder. Comparative Example 3 therefore failed to provide any sintered body of high density.

EXAMPLE 4-5 AND COMPARATIVE EXAMPLES 4-5

In a manner similar to Examples 1-3, each green body was formed and then subjected to debinding. Thereafter, the C/O molar ratio in the green body was adjusted to 0.2-4.0.

The thus-debound body was then sintered in a similar manner as in Examples 1–3, followed by the determination of the density ratio and the analyses of the C and 0 contents in the resultant sintered body.

The results are summarized in Table 2.

Examples 4 and 5 gave sintered bodies of high density and low impurity, because the C/O molar ratios fell within the range specified in this invention.

In Comparative Example 4, the C/O molar ratio was unduly small. It appears that the 0 content was too high and an oxid remained and impaired the attempted density increase.

In Comparative Example 5, the C/O molar ratio was unduly large. It appears that the content of remaining C was too high and unreacted C still remained at the high level in the sintered final body even after the reducing reaction.

winding was applied to the specimen thus prepared, and its magnetic characteristics and electrical resistivity were measured by an automatic flux measuring and recording instrument. The results are also given in Table 3.

In each of Run Nos. 1-1 to 1-5 given in Table 3, the contents of C and 0 in the debound body were adjusted by controlling the heating temperature in a range of 350°–650° C. in a hydrogen atmosphere whose dew point was 0° C., followed by first-stage sintering and second-stage sintering.

It is appreciated from Run Nos. 1-1 to 1-5 of Table 3 that magnetic characteristics were deteriorated when the contents of C and 0 exceeded 0.03 wt. % and 0.5 wt. % respectively (Comparative Examples 6 and 7). Further, when the content of 0 was unduly low (Comparative Example 6), it was unable to lower the content of C

TABLE 1

| | Average particle size of powdered raw material, μm | C/O molar ratio in debound body | First-stage sintering temperature, °C. | Density ratio of sintered body, % | C content in sintered body, wt % | O content in sintered body, wt % |
|---|---|---|---|---|---|---|
| Example 1 | 10 | 0.7 | 1080 | 96.0 | 0.05 | 0.31 |
| Example 2 | 10 | 0.7 | 1150 | 96.4 | 0.04 | 0.28 |
| Example 3 | 25 | 0.8 | 1150 | 95.2 | 0.03 | 0.25 |
| Comp. Ex. 1 | 10 | 0.7 | 1000 | 90.1 | 0.27 | 0.43 |
| Comp. Ex. 2 | 10 | 0.7 | 1250 | 90.3 | 0.26 | 0.51 |
| Comp. Ex. 3 | 35 | 0.5 | 1150 | 89.5 | 0.08 | 0.34 |

TABLE 2

| | C/O molar ratio in debound body | Density ratio of sintered body, % | C Content in sintered body, wt % | O Content in sintered body, wt % |
|---|---|---|---|---|
| Example 4 | 1.2 | 96.3 | 0.05 | 0.23 |
| Example 5 | 2.4 | 95.2 | 0.02 | 0.22 |
| Comp. Ex. 4 | 0.2 | 88.4 | 0.05 | 0.54 |
| Comp. Ex. 5 | 4.0 | 92.1 | 0.31 | 0.11 |

By using as a raw material a powder having an average particle size not greater than 30μm, conducting C/O adjustment of a green body in a conventional vacuum furnace before sintering and applying in combination low-temperature sintering under reduced pressure and high-temperature sintering, this invention has made it possible to produce sintered Ti bodies of low C and 0 contents and high density. It is hence possible to produce sintered Ti parts at a low cost and excellent productivity.

EXAMPLES 6–21 AND COMPARATIVE EXAMPLES 6–12

Each of the powdered raw materials shown in Table 3 was added with its corresponding binder also given in Table 3. After kneading the resultant mixture into a compound by a dispersion mixer, the compound was granulated to prepare an injection-molding feed-stock. The feed-stock was then formed into a ring-shaped green body having an outer diameter of 53 mm, an inner diameter of 41 mm and a height of 5 mm by an injection molding machine. The green body was then heated to 600° C. at a rate of 5° C./hr in nitrogen gas, at which it was maintained for 30 minutes to apply a debinding treatment.

Next, the debound body was then subjected to first-stage sintering and second-stage sintering under the corresponding conditions indicated in Table 3. The chemical composition and density ratio of the thus-obtained sintered body were measured. Further, a so that magnetic characteristics were deteriorated extremely. However, excellent magnetic characteristics were obtained when the contents of C and 0 were within their corresponding ranges specified in this invention (Examples 6–10).

When the temperature of the first-stage sintering was higher than the upper limit specified in this invention (Comparative Example 9) or lower than the lower limit defined in this invention (Comparative Example 10), the content of C was higher than the upper limit defined in this invention so that magnetic characteristics were deteriorated.

When the temperature of the second-stage sintering was not higher by at least 50° C. than the temperature of the first-stage sintering (Comparative Example 8), the low density ratio was only available so that excellent magnetic characteristics were not obtained.

When pressure-assisted sintering is effected in the second-stage sintering, no effects can be brought about when the pressure is lower than 30 atm (Comparative Example 11). Further, when the average particle size of the raw material exceeds 25 μm (Comparative Example 12), no advantage can be brought about. On the other hand, particle sizes smaller than 10μm (Example 16) cannot draw out the effects of this invention fully.

The density ratios of the sintered bodies subjected to pressure-assisted sintering at 30 atm or higher (Invention Examples 16–21) were all found higher than those of the bodies sintered under normal pressure (Examples 6–15).

TABLE 3

| Run No. | Powdered raw material Constituent powder Average particle size, μm, in parentheses | Average particle size, μm | Binder Amount added, wt %, in parentheses | First-stage sintering Atmosphere | First-stage sintering Temperature, °C | Second-stage sintering Atmosphere | Second-stage sintering Temperature, °C | Si content, wt % | O content, wt % | C content, wt % |
|---|---|---|---|---|---|---|---|---|---|---|
| 1-1 | | 4.9 | Wax type (10) | 0.001 $T_{orr}$ | 1155 | 1 atm Ar | 1300 | 3.5 | 0.44 | 0.01 |
| 1-2 | | 4.8 | Wax type (10) | 0.001 $T_{orr}$ | 1155 | 1 atm Ar | 1300 | 3.5 | 0.34 | 0.02 |
| 1-3 | | 4.9 | Wax type (10) | 0.001 $T_{orr}$ | 1155 | 1 atm Ar | 1300 | 3.5 | 0.33 | 0.03 |
| 1-4 | Carbonyl Fe powder | 4.9 | Wax type (10) | 0.001 $T_{orr}$ | 1155 | 1 atm Ar | 1300 | 3.5 | 0.02 | 0.11 |
| 1-5 | (4.8) | 4.8 | Wax type (10) | 0.001 $T_{orr}$ | 1155 | 1 atm Ar | 1300 | 3.5 | 0.45 | 0.02 |
| 1-6 | + ground Fe-44% Si | 4.9 | Wax type (10) | 0.001 $T_{orr}$ | 1155 | 1 atm Ar | 1300 | 3.5 | 0.05 | 0.03 |
| 1-7 | powder (6.9) | 4.9 | Wax type (10) | 0.001 $T_{orr}$ | 1155 | 1 atm Ar | 1300 | 3.5 | 0.10 | 0.02 |
| 1-8 | | 4.8 | Wax type (10) | 0.001 $T_{orr}$ | 1155 | 1 atm Ar | 1300 | 1.7 | 0.55 | 0.02 |
| 1-9 | | 5.0 | Wax type (10) | 0.001 $T_{orr}$ | 1155 | 1 atm Ar | 1300 | 6.3 | 0.38 | 0.02 |
| 1-10 | | 4.9 | Wax type (10) | $H_2$ | 1200 | $H_2$ | 1275 | 3.5 | 0.32 | 0.02 |
| 1-11 | | 4.9 | Wax type (10) | 0.001 $T_{orr}$ | 1155 | 1 atm Ar | 1800 | 3.5 | 0.30 | 0.02 |
| 2-1 | Atomized Fe—Si powder | 9.5 | Resin type (9) | 0.001 $T_{orr}$ | 1000 | 1 atm Ar | 1300 | 4.5 | 0.10 | 0.12 |
| 2-2 | Atomized Fe—Si powder | 9.5 | Resin type (9) | 0.001 $T_{orr}$ | 1100 | 1 atm Ar | 1300 | 4.5 | 0.37 | 0.02 |
| 2-3 | Atomized Fe—Si powder | 9.5 | Resin type (9) | 0.001 $T_{orr}$ | 1200 | 1 atm Ar | 1200 | 4.5 | 0.41 | 0.02 |
| 2-4 | Atomized Fe—Si powder | 9.5 | Resin type (9) | 0.001 $T_{orr}$ | 1300 | 1 atm Ar | 1300 | 4.5 | 0.45 | 0.04 |
| 3-1 | Atomized Fe—Si powder | 9.5 | Resin type (9) | 0.001 $T_{orr}$ | 1145 | 150 atm Ar | 1300 | 3.3 | 0.35 | 0.02 |
| 3-2 | Atomized Fe—Si powder | 11.3 | Resin type (9) | 0.001 $T_{orr}$ | 1000 | 150 atm Ar | 1300 | 3.3 | 0.31 | 0.02 |
| 3-3 | Atomized Fe—Si powder | 18.2 | Resin type (9) | 0.001 $T_{orr}$ | 1000 | 150 atm Ar | 1300 | 3.3 | 0.29 | 0.01 |
| 3-4 | Atomized Fe—Si powder | 18.2 | Resin type (9) | 0.001 $T_{orr}$ | 1000 | 25 atm Ar | 1300 | 3.3 | 0.25 | 0.02 |
| 3-5 | Atomized Fe—Si powder | 18.2 | Resin type (9) | 0.001 $T_{orr}$ | 1000 | 30 atm Ar | 1300 | 3.3 | 0.29 | 0.01 |
| 3-6 | Atomized Fe—Si powder | 21.9 | Resin type (9) | 0.001 $T_{orr}$ | 1000 | 150 atm Ar | 1300 | 3.3 | 0.25 | 0.01 |
| 3-7 | Atomized Fe—Si powder | 28.2 | Resin type (9) | 0.001 $T_{orr}$ | 1000 | 150 atm Ar | 1300 | 3.3 | 0.24 | 0.01 |
| 3-8 | Same as Nos. 1-1 to 1-11 | 4.9 | Resin type (9) | 0.001 $T_{orr}$ | 1000 | 150 atm $N_2$ | 1300 | 6.2 | 0.37 | 0.02 |

| Run No. | Density ratio, % | $B_{20}$, kG | Hc, Oe | $\mu_{max}$, — | Electrical resistivity, μΩcm | Remarks |
|---|---|---|---|---|---|---|
| 1-1 | 95.8 | 14.2 | 0.4 | 3300 | 48 | Example 6 |
| 1-2 | 95.6 | 14.2 | 0.4 | 3200 | 48 | Example 7 |
| 1-3 | 95.7 | 14.2 | 0.7 | 3000 | 48 | Example 8 |
| 1-4 | 95.7 | 13.8 | 1.5 | 1300 | 47 | Comp. Ex. 6 |
| 1-5 | 95.6 | 13.9 | 0.7 | 2500 | 49 | Comp. Ex. 7 |
| 1-6 | 95.7 | 14.2 | 0.6 | 3100 | 48 | Example 9 |
| 1-7 | 95.7 | 14.2 | 0.4 | 3200 | 48 | Example 10 |
| 1-8 | 95.3 | 15.2 | 0.4 | 2300 | 31 | Example 11 |
| 1-9 | 95.9 | 12.8 | 0.2 | 7200 | 87 | Example 12 |
| 1-10 | 95.3 | 14.2 | 0.4 | 3100 | 48 | Example 13 |
| 1-11 | 92.8 | 13.5 | 1.0 | 1800 | 50 | Comp. Ex. 8 |
| 2-1 | 95.3 | 13.0 | 1.6 | 1200 | 58 | Comp. Ex. 9 |
| 2-2 | 95.3 | 13.4 | 0.4 | 3400 | 61 | Example 14 |
| 2-3 | 95.6 | 13.4 | 0.4 | 3300 | 59 | Example 15 |
| 2-4 | 95.4 | 13.1 | 0.8 | 2300 | 59 | Comp. Ex. 10 |
| 3-1 | 96.7 | 14.4 | 0.3 | 3800 | 42 | Example 16 |
| 3-2 | 97.8 | 14.6 | 0.3 | 4500 | 42 | Example 17 |
| 3-3 | 98.5 | 14.7 | 0.3 | 5100 | 42 | Example 18 |
| 3-4 | 94.5 | 14.1 | 0.7 | 2800 | 43 | Comp. Ex. 11 |
| 3-5 | 96.1 | 14.4 | 0.4 | 3500 | 42 | Example 19 |
| 3-6 | 97.5 | 14.6 | 0.3 | 5000 | 42 | Example 20 |
| 3-7 | 89.0 | 13.2 | 1.2 | 1400 | 46 | Comp. Ex. 12 |
| 3-8 | 98.3 | 13.5 | 0.2 | 4900 | 85 | Example 21 |

This invention can provide sintered Fe-Si magnetic bodies of excellent a.c. magnetic characteristics by using an injection molding method and eliminating organic-binder-derived C without extreme oxidation.

We claim:

1. A sintered magnetic body of the Fe-Si type consisting essentially of 1.5-6.5 wt. % of Si, up to 0.5 wt./T of O, up to 0.03 wt. % of C, and the balance of Fe and imperative impurities and having a density ratio of at least 95%.

2. A process for the production of a sintered magnetic body of the Fe-Si type, which comprises the following steps:

(i) mixing and kneading at least one powder selected from the group which consists of one or more Fe-Si alloy powders, an Fe powder and a Si powder with a binder into a compound, to give a final composition which comprises 1.5-6.5 wt. % of Si and the balance substantially of Fe, said alloy and metal powders having an average particle size of 3-25 μm;

(ii) injection molding the compound into a green body;

(iii) debinding the green body to form a debound body; and (iv) subjecting the debound body to a first stage sintering step at 1,050-1,250° C. in a reducing atmosphere or in a reduced-pressure atmosphere not higher than 0.1 Torr, and then subjecting the body to a second-stage sintering step at a temperature at least 50° C. higher than the temperature of the first-stage sintering step.

3. The process as claimed in claim 2, further comprising the step of adjusting the C/O molar ratio of the debound body to 0.5-3.0 before conducting the first-stage sintering step.

4. The process as claimed in claim 2, wherein the second-stage sintering step is conducted in an inert gas atmosphere of at least 30 atm.

5. The process as claimed in claim 4, wherein the alloy and metal powders have an average particle size of 10-25 μm.

* * * * *

UNITED STATES PATENT AND TRADEMARK OFFICE
CERTIFICATE OF CORRECTION

PATENT NO. : 5,067,979

DATED : November 26, 1991

INVENTOR(S) : Yoshisato Kiyota et al

It is certified that error appears in the above-identified patent and that said Letters Patent is hereby corrected as shown below:

On the title page, in the Abstract, line 10, after "a" insert --reducing or--, and line 12, please change "400" to --1400--.

Column 1, line 13, after "lent" delete "a.c."; and
line 17. please change "FeCo" to --Fe-Co--.

Column 7, line 24, delete ":", second occurrence and insert therefor --;--.

Column 9, line 11, please change "oxid" to --oxide--.

Columns 11 and 12, in Table 3, Run No. 1-11, under the subheading "Temperature, °C", under "Second-Stage Sintering", please change "1800" to --1180--;
in Run No. 2-3, under the heading "Second-Stage Sintering", under the subheading "Temperature, °C", please change "1200" to --1300--; and
in Runs 3-2, 3-3, 3-4, 3-5, 3-6, 3-7 and 3-8, under the heading "First-Stage Sintering", subheading "Temperature, °C", please change "1000" in all seven occurrences to --1145--.

UNITED STATES PATENT AND TRADEMARK OFFICE
CERTIFICATE OF CORRECTION

PATENT NO. : 5,067,979

DATED : November 26, 1991

INVENTOR(S) : Yoshisato Kiyota, et al.

It is certified that error appears in the above-identified patent and that said Letters Patent is hereby corrected as shown below:

Column 11, line 57, change "wt./T" to --wt./%--.

Signed and Sealed this

Twenty-fifth Day of May, 1993

Attest:

MICHAEL K. KIRK

Attesting Officer     Acting Commissioner of Patents and Trademarks